(12) United States Patent
Mazzola et al.

(10) Patent No.: US 8,598,232 B2
(45) Date of Patent: Dec. 3, 2013

(54) PROCESS FOR THE PREPARATION OF NON-GENOTOXIC DIACETYLRHEIN (DIACEREIN) AND FORMULATIONS COMPRISING NON-GENOTOXIC DIACETYLRHEIN

(75) Inventors: Alessandro Mazzola, Milan (IT); Silvia Moiana, Cantu-Como (IT)

(73) Assignee: Evultis SA, Lugano (CH)

( * ) Notice: Subject to any disclaimer, the term of this patent is extended or adjusted under 35 U.S.C. 154(b) by 226 days.

(21) Appl. No.: 13/133,526

(22) PCT Filed: Nov. 3, 2009

(86) PCT No.: PCT/EP2009/064555
§ 371 (c)(1),
(2), (4) Date: Jun. 8, 2011

(87) PCT Pub. No.: WO2010/000879
PCT Pub. Date: Jan. 7, 2010

(65) Prior Publication Data
US 2011/0245341 A1    Oct. 6, 2011

(30) Foreign Application Priority Data

Dec. 9, 2008  (EP) ..................................... 08305906
Feb. 16, 2009  (EP) ..................................... 09152936

(51) Int. Cl.
*A61K 31/225*    (2006.01)
(52) U.S. Cl.
USPC ....................................................... 514/548
(58) Field of Classification Search
None
See application file for complete search history.

(56) References Cited

U.S. PATENT DOCUMENTS 5,756,782 A * 5/1998 Cohen ........................... 552/262
6,624,192 B1    9/2003 Carcasona et al.

FOREIGN PATENT DOCUMENTS

EP    0928781 A1    7/1999
WO    WO 2004/050601 A2    6/2004

OTHER PUBLICATIONS

International Search Report dated Feb. 12, 2010 for PCT/EP2009/064555.

* cited by examiner

*Primary Examiner* — Craig Ricci
(74) *Attorney, Agent, or Firm* — Birch, Stewart, Kolasch & Birch, LLP

(57) ABSTRACT

The present invention is directed to a process for producing non-genotoxic Diacetylrhein (Diacerein), comprising: i) transformation of raw Diacerein (or raw Rhein), into a water-soluble salt; ii) adsorption of the salt Diacerein (or Rhein) solution on a hydrophobic resin; iii) washing with an appropriate solvent to eliminate the impurities (in particular the genotoxic impurities); iv) elution to recover Diacereinor Rhein; v) if the process is applied to Rhein, its transformation to Diacerein by acetylation; vi) acidification of purified Diacerein and its recovery, and drying. The invention is also directed to non-genotoxic Diacerein obtained by the process of the invention, in which the total content of genotoxic impurities is below 1 ppm, and suitable for the preparation of pharmaceutical formulations, in particular capsules, for human and veterinary use, in agreement with the current Health Authorities request.

22 Claims, No Drawings

PROCESS FOR THE PREPARATION OF NON-GENOTOXIC DIACETYLRHEIN (DIACEREIN) AND FORMULATIONS COMPRISING NON-GENOTOXIC DIACETYLRHEIN

The present invention concerns a new process for the preparation of Diacetylrhein (Diacerein), with a high degree of purity, specifically with a low content of genotoxic impurities. These characteristics allow the use of non genotoxic Diacerein in pharmaceutical formulations for human and veterinary applications.

Diacerein (chemical name: 1,8-diacetoxy-3-carboxyanthraquinone) is a molecule having anti-inflammatory activity (in particular anti-free-radicals activity) and as such can be used in the prevention and treatment of various pathological states, in particular those concerning degradation of cartilage, for example in certain forms of arthritis and osteoarthritis.

Chemically, Diacerein has the following structure:

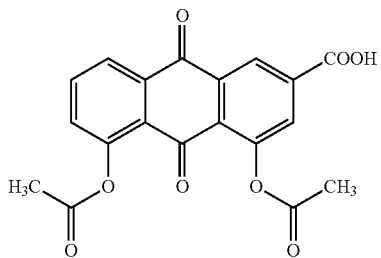 [SMILES: CC(=O)Oc1cccc2c1C(=O)c1c(OC(C)=O)cc(C(=O)O)cc1C2=O]

The raw materials for the preparation of Diacerein are vegetable extracts deriving from different species of plants containing the glycosilate-based anthraquinone structure; in particular, Senna or Aloe extracts are the most appropriated. In the following document, the nomenclature used will refer to products obtained from Aloe extracts, although the method could be applied to all vegetable extracts, deriving from any species of plant containing products that can be transformed into Diacerein.

Usually, the 3-carboxy-1,8-diacetylated anthraquinone product is obtained by an oxidative degradation of the sugars contained in the first-extraction products by different agents such as: chromic anhydride (DE A-4.120.989 and DE A-120.990) or $FeCl_3$ (WO96/30034). After this oxidation step, the corresponding anthraquinone tri-alcohol (Aloemodine) is isolated; the next step is the acetylation reaction of the phenolic and alcoholic groups present in the Aloemodine with the production of the so-called triacetate (Aloemodine triacetate). Diacerein is achieved by transforming the methylene-alcoholic group ($-CH_2OH$) in position 3 into the corresponding carboxylic group by means of oxidation.

An alternative process to obtain crude Diacerein always from Aloin, is the acetylation of Aloin followed by oxidation with chromic anhydride.

As stated above, such steps belong to the state of the art, as described in different patents.

It was already known that crude Diacerein contains impurities, which have to be eliminated.

Many purification processes are described by various authors. Some patents describe the extraction, with mixtures of organic solvents not particularly mixable (liquid/liquid extraction), sometimes in counter-current (EP 520 414) in the presence of organic bases—such as triethylamine—which increase the solubility of the products. Other authors carry out successive precipitations of different inorganic salts, in various solvent mixtures (WO 2004/050601).

Depending on the process applied, the final product presents a degree of purity that is often unsuitable for oral pharmaceutical humans and veterinary applications, requiring further purification steps with an obvious reduction in process yield. In particular, these processes do not lead to a non-genotoxic Diacerein, in particular to a high purified and non-genotoxic Diacerein.

In the following, the terms "genotoxic impurities" refer to compounds that have the potential to damage DNA at any level of exposure, said damage leading/contributing to tumour development.

The terms "non genotoxic impurities" refer to compounds that do not have the potential to damage DNA but are nevertheless toxic for humans.

Depending from the vegetables extract used as raw material and applied manufacturing method, different genotoxic impurities could be present in the final product. Among these impurities, the following products are relevant, due to their genotoxic activity: Emodine, mono-acetyl-Emodine, di-acetyl-Emodine, tri-acetyl-Emodine, Aloemodine, mono-acetyl-Aloemodine, di-acetyl-Aloemodine and tri-acetyl-Aloemodine.

When Diacerein is obtained from Aloe, the genotoxic impurities are Aloemodine, and its mono, di- and tri-acetylated derivatives, which have the following structure:

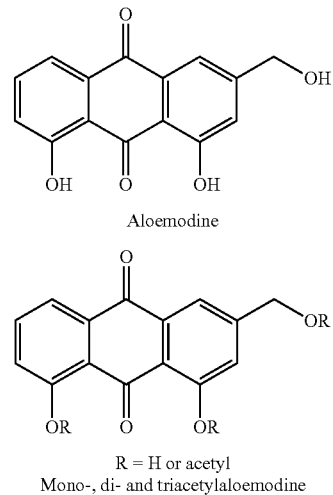

Aloemodine

R = H or acetyl
Mono-, di- and triacetylaloemodine and Emodine, and its mono, di- and tri-acetylated derivatives, which have the following structure:

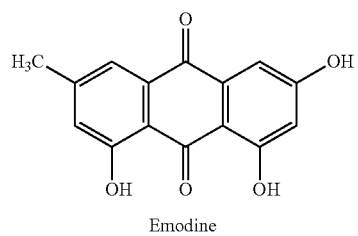

Emodine

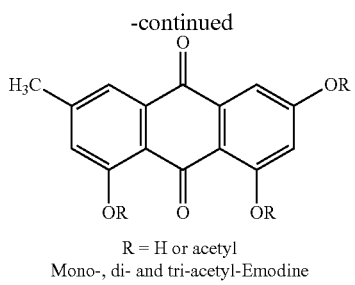

R = H or acetyl
Mono-, di- and tri-acetyl-Emodine

The other impurities toxic for humans are: 1,8-Danthrone, Rhein, mono-acetyl-Rhein I, mono-acetyl-Rhein II, which have the following structure:

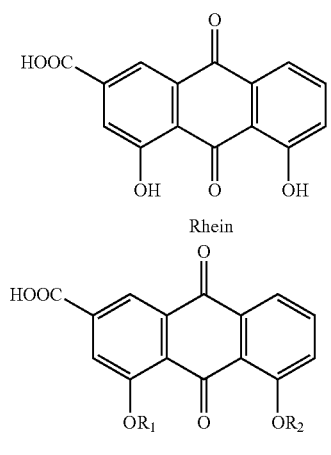

Rhein

Mono-acetyl-Rhein I; $R_1$ = acetyl $R_2$ = H
Mono-acetyl-Rhein II; $R_1$ = H $R_2$ = acetyl

1,8-Dathron and in addition N,N-dimethylformamide, acetone, triethylamine, ethanol, acetic acid, chromium and other heavy metals including chromium.

Today, for all the new drugs, Health Authorities requires the identification and the quantification of genotoxic compounds; the maximal accepted amount for genotoxic impurities being fixed by very precise limits.

The ICH guidelines (EMEA/CHMP/QWP/251344/2006), require a total genotoxic impurities content (in term of TTC: Threshold of Toxicological Concern) below to 15 ppm.

This limit is more low than those described in the patents submitted before 2006 (example EP 520 414).

Due to the new requirements of Health Agencies on genotoxic compounds, the presence of these impurities make today inappropriate the use of non high purified Diacerein as an active ingredient in pharmaceutical preparations for human and veterinary uses. For this reason, it was necessary to develop a new purification process, which will allow obtaining a high purified Diacerein, it means a Diacerein free of these genotoxic and non-genotoxic impurities.

Surprisingly, it has now been found that appropriate resins can be used to purify Diacerein, with elimination also of the specific genotoxic compounds (Aloemodine and mono-, di- and tri-acetyl-derivatives, in particular tri-acetyl-Aloemodine, and also Emodine, and mono-, di-, and tri-acetyl-derivatives). This new purification process can be implemented on Diacerein as such or in its de-acetylated form (Rhein). It involves the use of appropriate resins to selectively separate Diacerein, from the impurities. This process allows obtaining non genotoxic Diacerein: preferably genotoxic impurities are not detectable by usual analytical methods (it means less than 1 ppm). The non-genotoxic Diacerein thus obtained can than be used for pharmaceutical formulations for human and veterinary applications. These formulations are in particular appropriate for oral administration.

Thus, an object of the invention is a process for producing non genotoxic Diacerein, in particular high purified non genotoxic Diacerein.

The process of the invention is applied to Diacerein as such or to Rhein. It comprises the following successive steps:
 a. transforming raw Diacerein or raw Rhein, into a water-soluble salt thereof; then
 b. dissolving said salt in water;
 c. adsorbing Diacerein or Rhein on a hydrophobic resin by passage of the aqueous solution obtained in step b. through a column filled with said hydrophobic resin;
 d. after step c., desorbing the impurities by flowing an appropriate organic solution through said column and recovering the organic solution which contains the genotoxic and non genotoxic impurities;
 e. after step d., eluting Diacerein or Rhein by flowing an hydro alcoholic solution through said column and, recovering the hydro alcoholic solution which contains high purified and non-genotoxic Diacerein or Rhein salt;
 f. acidifying the hydro alcoholic solution recovered after step e.;
 g. recovering and drying non genotoxic Diacerein or Rhein.

When the starting product is Rhein, the process comprises, after step f. and before step g., an additional step consisting in transforming Rhein in Diacerein by acetylation.

The terms "non genotoxic Diacerein" means a Diacerein in which the total genotoxic impurities content is below 1 ppm. Furthermore the other impurities are at a very low levels, in particular
 below 1% w/w for Rhein, mono-acetyl-Rhein I, mono-acetyl-Rhein II;
 below 1 ppm for 1,8-Danthrone, in particular below 0.1 ppm;
 below 10 ppm for heavy metals including chromium;
 below 500 ppm for solvents.

The raw Diacerein, used in step a., could have different extraction origins. In particular,
 Process of the present invention is applied to:
  the raw material obtained from Aloe which contains Diacerein and impurities (in particular genotoxic impurities as Aloemodine, Emodine and their derivatives), following Type A process described below;
  the mixture obtained by total deacetylation of the above described raw material following Type B Process. De-acetylation to obtain Rhein is performed using known methods, such as those described in WO 96/30034.

The process could start from raw Diacerein or Rhein containing significant amounts of impurities, in particular genotoxic impurities.

In a particular embodiment of the invention, when the content of genotoxic impurities is too high (in particular much more than 500 or 600 ppm), at least one previous crystallisation is performed before implementing the process of the invention. The crystallisation solvent can for example be N,N-dimethylformamide (DMF).

Surprisingly, the inventors have discovered that lipophylic resins could be used to efficiently separate Diacerein or Rhein from the impurities (particularly the genotoxic impurities) deriving from the extraction/modification of the initial plant extract. Without being bond by any theory, the inventors think that this could be explained by their difference in their degree of lipophylicity/hydrophylicity, correlated to structural differences (for example, presence of acetylated phenolic and primary alcoholic groups or not, or phenolic and acetylated groups or not, and salifiable carboxylic groups).

Water-Soluble Salt:

Type A Process: The first step of the process (a.) is to salify the raw Diacerein to obtain a salt of Diacerein which is soluble in water. The water soluble salt of Diacerein is preferably an inorganic salt of Diacerein, more preferably a salt of Diacerein with an alkali metal. In a preferred embodiment, the salt of Diacerein is a potassium salt of Diacerein or a sodium salt of Diacerein. The solubility of potassium salt of Diacerein is around 1 g/50 ml of water at neutral pH (pH=7).

Type B Process: The first step of the process (a.) is to salify the raw Rhein to obtain a salt of Rhein which is soluble in water. The water soluble salt of Rhein is preferably an inorganic salt of Rhein, more preferably a salt of Rhein with an alkali metal. In a preferred embodiment, the salt of Rhein is a potassium salt of Rhein or a sodium salt of Rhein.

Hydrophobic Resin:

The resin used in the process of the invention is a hydrophobic resin.

Such hydrophobic resin is preferably a polymer-type, wherein said polymer backbone does not comprise hydrophilic functional groups (such as OH, COOH, $NH_2$ ... ). The polymer backbone is advantageously an hydrocarbon backbone (constituted from C and H atoms), which may presents hydrophobic-substituents.

A hydrophobic compound does not form hydrogen bounds with the molecules of water. A hydrophobic compound is often a non-polar compound but some hydrophobic compounds can be slightly polar compounds.

As example of suitable polymer, a copolymer of styrene and divinylbenzene (PS-DVB) can be considered. Said copolymer may be substituted on the benzene by halogen atoms (in particular by bromine atom).

According to a preferred embodiment, the resin is not only hydrophobic but is also porous, even more highly porous.

The porosity of the resin may for example be defined by its pore volume, which is preferably above 1 ml/g, more preferably between 1 ml/g and 2.5 ml/g.

The porous hydrophobic resin has advantageously an important specific surface area, which is preferably above 550 $m^2$/g. In a particular embodiment, the specific area is between 550 $m^2$/g and 1300 $m^2$/g, more preferably between 590 $m^2$/g and 1200 $m^2$/g.

The resin is preferably under the form of particles, whose size may range from 50 μm to 700 μm. In one particular embodiment, the particle size range is between 250 μm and 700 μm, advantageously between 250 μm and 600 μm. In another particular embodiment, the particle size ranges between 50 μm and 150 μm. The resin may furthermore have a tendency to swell. In a particular embodiment, a resin having a water retention capacity ranging from 40% to 70% is used, advantageously from 45% to 55%.

As non limiting examples of appropriate commercial resins, the following products could be mentioned: DIAION® (HP20, HP20SS, HP21, HP2MG) or SEPABEADS® (SP70, SP700, SP825, SP850, SP20SS, SP207, SP207SS) or MCI® GEL (CHP20A/Y/P, CHP55A/Y) or other PS-DVB resins.

Since the purification process is based on interactions between the compounds (Diacerein or Rhein and impurities) and the resin, a sufficient contact time between them is essential. The person skilled in the art, on the basis of producer instructions and preliminary tests, is able to define the column dimensions (length, diameter), the ratio between the amount of the product to be purified and the resin, and other parameters (solvent, flow, pressure ... ) to perform the purification process. The person skilled in the art will also take into consideration the quantity of impurities contained in the raw Diacerein or Rhein.

Separation Process:

The water soluble salt of raw Diacerein (or Rhein) is dissolved in water (step b.) and then the resulting aqueous solution is percolated through a column filled with a hydrophobic resin (step c.) prepared according to the instructions described by the producer and by preliminary experiment results.

In the following, the column filled with a hydrophobic resin is also called a "resin bed". The resin can also be designated by the use of the term "adsorbent".

In a preferred embodiment, the purification process starts with the percolation of the Diacerein (or Rhein) sodium salt aqueous solution, through the resin bed, at the appropriate speed, chosen by preliminary studies. The percolation of the aqueous solution, through the resin bed, results on different interactions between the molecules (Diacerein- or Rhein- and impurities) and the adsorbent; the interaction forces with the adsorbent being different for Diacerein (or Rhein) and impurities. This first step is called "adsorption step".

During the adsorption step, Diacerein (or Rhein) and impurities are adsorbed on the resin. The aqueous solution from the column does not contain significant amounts of Diacerein (or Rhein) and impurities any more.

After the adsorption step, the resin bed is washed with an appropriate organic solvent, in particular polar organic solvent such as acetone or acetonitrile. This second step is called "washing step" (step d.). This washing step will allow desorption of the impurities with the consequence that the organic solution from the column contains all the impurities but does not contain significant amounts of Diacerein (or Rhein). After the washing step, the only compounds still adsorbed on the resin are Diacerein or Rhein.

The following step is called "elution step" (step e.): the elution solvent (also called eluant) is percolated through the column, one or many times (at least two times). This elution step will allow the recovery of Diacerein or Rhein from the column.

In a preferred embodiment, the eluant is a mixture of water and alcohol, the alcohol being preferably a $C_1$-$C_4$ alcohol, more preferably ethanol or methanol. The alcohol/water ratio preferably ranges from 10%/90% to 60%/40% (the percentages being expressed in weight compared to the total weight of water and alcohol). In a preferred embodiment of the invention, at least two elution steps are performed with hydro alcoholic solutions, using a gradient of water/alcohol, starting from the lower percentage of alcohol. In a more preferred embodiment of the invention, the first elution is performed by an ethanol or methanol/water mixture in about 20/80 ratio and the last elution is performed by an ethanol or methanol/water mixture in about 60/40 ratio.

The number of elution steps, which depends on the nature of the resin and of the eluant, can easily be determined by the person skilled in the art with preliminary tests on selected resin.

The first fraction of eluates which contain the Diacerein or the Rhein salts is recovered and if appropriate, also the following fractions, containing additional Diacerein or Rhein. The detection and the quantification of Diacerein (or Rhein) in the eluted fractions are determinated by HPLC using reference standards and related retention times.

When Diacerein or Rhein from Aloe is purified by this process, the HPLC method can have for example the following main characteristics:

Column: Supelcosil LC-ABZ® 150×4.6 mm, 5 µm (Supelco)
Flow rate: 1.5 ml/min
Detector: 254 nm
Column temperature: 40° C.
Injection volume: 20 µl
Run Time: 25 min
LOD: 0.45 ppm (w/w) with regards to Diacerein
LOQ: 1.35 ppm (w/w) with regards to Diacerein More precise data can be obtained by HPLC coupled with a mass spectrometry detector.

The recovered fractions, containing Diacerein (or Rhein) salts, are then acidified by well-known methods in order to obtain the Diacerein (or Rhein) as free carboxylic acid (step f.). Rhein is transformed into Diacerein by described methods. Afterward, the high purified and non-genotoxic Diacerein is recovered and dried by usual method (step g.).

Diacerein in form of the free carboxylic acid can be recovered by acidification with an appropriate organic or inorganic acid (preferably a diluted strong acid such as $H_2SO_4$ 1M), with subsequent precipitation of the Diacerein, its filtration under vacuum, followed by washings with water. In the case of Rhein, after acidification with an appropriate organic or inorganic acid (preferably a diluted strong acid such as $H_2SO_4$ 1M), the precipitate is filtered and, after complete drying, is dissolved in anhydrous pyridine and acetic anhydride (as described by well-know methods). Once reaction is completed, the addition of water and ice to the mixture causes the precipitation of high purified and non-genotoxic Diacerein and the dissolution of the present salts. The final product is recovered by filtration, preferably under vacuum or centrifugation, followed by washings with water.

The degree of purity of the final product is detected by HPLC following for example the chromatographic conditions described above.

The genotoxic impurities content is advantageously below the detection threshold of this method, which means that the content is below than 1 ppm.

The non genotoxic impurities content is advantageously
below 1% w/w for Rhein, mono-acetyl-Rhein I, mono-acetyl-Rhein II;
below 1 ppm for 1,8-Danthrone, in particular below 0.1 ppm;
below 10 ppm for heavy metals including chromium;
below 500 ppm for solvents.

In particular, the specifications of the high purified non genotoxic Diacerein of the invention for the following impurities are:

Rhein derivatives and 1,8-Danthrone

| | |
|---|---|
| Rhein | Not more than 0.20% w/w |
| Mono-acetyl-Rhein I | Not more than 0.50% w/w |
| Mono-acetyl-Rhein II | Not more than 0.50% w/w |
| 1,8-Danthrone | Not more than 0.1 ppm |
| Each any unknown | Not more than 0.10% w/w |

Genotoxic impurities

| | |
|---|---|
| Aloemodine (sum of Aloemodine, mono-, di- and tri-acetyl-Aloemodine) | Not more than 1ppm |
| Tri-acetyl-Aloemodine | Not more than 0.2 ppm |
| Tri-acetyl-Emodine | Not more than 0.1 ppm |
| Emodine | Not more than 1 ppm |

Heavy metals and chromium

| | |
|---|---|
| Heavy metals: | Not more than 10 ppm |
| Chromium content: | Not more than 5 ppm |

Residual solvents

| | |
|---|---|
| N,N dimethylformamide | Not more than 500 ppm |
| Acetone | Not more than 50 ppm |
| Acetic acid | Not more than 50 ppm |
| Ethanol | Not more than 50 ppm |
| Triethylamine | Not more than 50 ppm |

The total yield of Processes A or B is on average around 75-90% referring to the raw Diacerein or raw Rhein content, in form of the free carboxylic acid, which may contain even more than 500-600 ppm of genotoxic impurities.

The invention is also directed to non-genotoxic Diacerein obtainable by the process of the invention. In said non-genotoxic Diacerein the total content of genotoxic impurities is below 1 ppm.

The invention also encompasses pharmaceutical formulations comprising as active ingredient said non-genotoxic Diacerein and pharmaceutically acceptable excipients, in particular non-genotoxic excipients. The formulations are preferably under a form suitable for an oral administration.

The invention relates in particular to capsules comprising as active ingredient the non-genotoxic Diacerein of the invention and non-genotoxic excipients. The excipients are advantageously lactose and magnesium stearate. The capsules are advantageously prepared by filling hard gelatine capsules with a homogenized powder mixture (formed by mixing the non genotoxic diacerein, in the powder form, with lactose and magnesium sterarate). One can for example use the Press-Fit™ technology (covering a tablet by two flexible gelcaps).

The high purified non-genotoxic Diacerein of the invention can be used as medicament, for human beings and animals. The medicament can be used for treating pathological states concerning degradation of cartilage, for example for treating arthritis and osteoarthritis.

The following examples, which in no way limit the scope of the invention, illustrate the preferred embodiments of the processes.

EXAMPLE 1

Use of SEPABEADS SP207® and HP20® Resins

Preparation of Potassium Salt of Raw Diacerein 50 g of raw Diacerein containing about 500 ppm of genotoxic impurities are suspended in 750 ml of acetone and 50 ml of water and, under magnetic agitation, 25 ml of triethylamine diluted in 100 ml of acetone, are added over a period of 3 hours, keeping pH not more than 7, until complete dissolution. The final solution obtained is treated at 18° C. with 32 g of potassium ethyl hexanoate in 260 ml of acetone. Salification agent is added over a period of 2 hours. A precipitate is formed; after filtration, the precipitate is washed with 500 ml of acetone and dried under vacuum at 40° C. for one night.

50 g of potassium salt of Diacerein are obtained.

Elution:

15 g of this product are dissolved in 750 ml of water. This solution, after filtration under vacuum, is percolated through a 4.5 cm-diameter 120 cm-high column, packed with 1.1 l of SEPABEADS® SP207® or DIAION HP20® (flow rate 20 ml/min).

The typical characteristics of SEPABEADS® SP207® and DIAION HP20® are given in the Table 1 below:

TABLE 1

Characteristics of SEPABEADS ® SP207 ® and DIAION HP20 ®

|  | SEPABEADS ® SP207 ® | DIAION HP20 ® |
| --- | --- | --- |
| Water retention % | 45-55 | 55-65 |
| Particle size 205 μm | 250-600 | 250-600 |
| Specific surface area (m²/g) | 590 | 590 |
| Specific gravity | 1.18 | 1.01 |
| Pore volume (ml/g) | 1.1 | 1.3 |
| Average pore radius (Å) | 120 | 260 |

Afterwards, the column is washed with a bed volume of acetone (flow rate 18-20 ml/min).

Four elution steps with ethanol/water mixture are performed to recover Diacerein potassium salt: the first elution is performed by using ethanol/water mixture 20%/80% (100 ml/400 ml) and the three last elutions by using ethanol/water mixture 60%/40% (300 ml/200 ml) (for each elution step the flow rate is about 15-20 ml/min).

The collected fractions, containing the product, are then brought to pH 2.5-3 with 10% sulphuric acid ($H_2SO_4$). The suspension is cooled to 20°-25° C. and stirred for a period of 30 minutes; the precipitate is recovered by filtration under vacuum, washed with 150 ml of hot water (45-50° C.) and 150 ml of acetone, and then dried under vacuum.

Around 11.5 g of Diacerein are obtained with both the cited resins, showing a genotoxic impurities content lower than 1 ppm detected by HPLC.

EXAMPLE 2

Use of DIAION HP2MG Resin

Preparation of Potassium Salt of Raw Diacerein 50 g of Diacerein containing about 500 ppm of genotoxic impurities are suspended in 750 ml of acetone and 50 ml of water and, under magnetic agitation, 25 ml of triethylamine diluted with 100 ml of acetone are added over a period of 3 hours keeping pH not more than 7, until complete dissolution. The obtained solution is treated with 32 g of potassium ethyl hexanoate in 260 ml of acetone, over a period of 2 hours. The obtained precipitate is filtered, washed with 500 ml of acetone and dried under vacuum at 40° C. for one night. 50 g of potassium Diacerein salt is obtained.

Elution:

25 g of potassium Diacerein salt are dissolved in 1250 ml of water. The solution, after filtration under vacuum, is percolated through a 10.0 cm-diameter and 110 cm high column, packed with 5.1 l of DIAION HP2MG® (flow rate 20 ml/min).

The typical characteristics of DIAION HP2MG® are given in the Table 2 below:

TABLE 2

Characteristics of DIAION HP2MG ®.

|  | DIAION HP2MG ® |
| --- | --- |
| Water retention % | 55-65 |
| Particle size 205 μm | 300-700 |
| Specific surface area (m²/g) | 570 |
| Specific gravity | 1.09 |
| Pore volume (ml/g) | 1.3 |
| Average pore radius (Å) | 240 |

The column is washed with a bed volume of acetone (flow rate 18-20 ml/min), followed by 4 elution steps: the first elution step using ethanol/water mixture 20%/80% (100 ml/400 ml) and the last three steps with ethanol/water 60%/40% (300 ml/200 ml) (for each elution step the flow rate is about 15-20 ml/min).

The collected fractions containing the product are then brought to pH 2.5-3.0 with sulphuric acid. The suspension is cooled to 20°-25° C. and stirring over a period of 30 minutes. The precipitate is filtrated under vacuum, washed with 300 ml of hot water (45°-50° C.) and 150 ml of acetone, and then dried under vacuum.

19.25 g of Diacerein are obtained, showing a genotoxic impurity content lower than 1 ppm.

EXAMPLE 3

5 g of raw Diacerein containing about 300 ppm of genotoxic impurities derivatives is dissolved in 40 ml of methanol and, under magnetic agitation, 40 ml of water and 5 g of KOH are added. In the presence of a condenser, heating to 60-65° C. is performed for 30 minutes; after this period, 35 ml of 6N HCL are added; dilution with about 35 ml of water is performed and the solution is boiled for about 30 minutes. After cooling, the suspension is filtered under vacuum, the residue washed with water and dried under vacuum at constant weight.

4.5 g of Rhein are thus obtained.

2 g of Rhein thus obtained are transformed into the corresponding potassium salt as described for the Diacerein in Example 1.

2 g of potassium salt of Rhein are dissolved in 200 ml of water (final pH of the solution 6.2). This solution, after filtration under vacuum, is percolated through a 7.5 cm-diameter 10 cm-high column, packed with 180 g of SEPABEADS® SP207® (flow rate 20 ml/min).

Washing with a volume corresponding to the volume of the column of acetone (flow rate 18-20 ml/min) and then elution with a water/ethanol mixture are performed until the complete elution of the Rhein. 4 elution steps are performed: the two first elutions are performed by using ethanol/water mixture 20%/80% and the two last elutions are performed by using ethanol/water mixture 60%/40% (for each elution step the flow rate is about 15-20 ml/min).

The fraction containing the Rhein is then brought to pH 4.5-5 with 10% sulphuric acid ($H_2SO_4$). The suspension is cooled to 5-10° C., the precipitate recovered by filtration under vacuum, washed with cold water and dried under vacuum.

The precipitate, after drying, is acetylated using pyridine and acetic anhydride in a ratio of 1:1 (alternatively, other conventional acetylating agents may be used).

After drying, 1.8 g of Diacerein are obtained, showing a content of genotoxic impurities lower than 1 ppm.

Analytical Determinations

HPLC Analysis for Diacerein, Mono-Acetyl-Rhein I, Mono-Acetyl-Rhein II and Rhein.
Column: Supercosil LC-ABZ 150×4.6 mm, 5 µm (Supelco)
Flow rate: 1.5 ml/min
Detector: 254 nm
Column temperature: 40° C.
Injection volume: 20 µl
Time: 25 min The method has been validated for linearity, specificity, precision, stability of the samples, quantitation and detection limits, and accuracy.

The specifications of the high purified non genotoxic Diacerein of the invention for the following impurities are:

| | |
|---|---|
| Rhein | Not more than 0.20% (our results from 0.0% to 0.05%) |
| Mono-acetyl-Rhein I | Not more than 0.50% (our results from 0.07% to 0.22%) |
| Mono-acetyl-Rhein II | Not more than 0.50% (our results from 0.11% to 0.21%) |
| Each any unknown | Not more than 0.10% (our results: absent) |

The corresponding retention times (RT) are:

| | |
|---|---|
| Diacerein | 4.4 min |
| Mono-acetyl-Rhein II | 5.8 min |
| Mono-acetyl-Rhein I | 7.0 min |
| Rhein | 10.5 min |

HPLC Analysis for Aloemodine (Sum of Aloemodine and Mono-, Di- and Tri-Acetyl-Aloemodine after Hydrolysis).
Column: Supercosil LC-ABZ 150×4.6 mm, 5 µm (Supelco)
Flow rate: 1.5 ml/min
Detector: 254 nm
Column temperature: 40° C.
Injection volume: 20 µl
Run Time: 20 min The method has been validated for linearity, specificity, precision, stability of the samples, quantitation and detection limits, and accuracy.

The specifications of the high purified non genotoxic Diacerein of the invention for the following impurities are:
Aloemodine Not more than 1 ppm (our results from 0 to 1 ppm) (sum of Aloemodine, mono-, di- and tri-acetyl-Aloemodine)

The corresponding retention time (RT) for Aloemodine is:

| | |
|---|---|
| Aloemodine | 12.3 min |

HPLC/LC-MS Analysis for Diacerein, Mono-Acetyl-Rhein I, Mono-Acetyl-Rhein II, Aloemodine, Tri-Acetyl-Aloemodine, Rhein, Tri-Acetyl-Emodine, Emodine, 1,8-Danthron.
Column: J. Sphere H80 ODS 4 µm, 250×4.6 mm (YMC) (or equivalent)
Flow rate: 0.8 ml/min
Detector: 254 nm
Injection volume: 20 µl
Run Time: 60 min The method has been validated for linearity, specificity, precision, stability of the samples, quantitation and detection limits, and accuracy.

The corresponding retention times (RT) are:

| | |
|---|---|
| Diacerein | 9.0 min |
| Mono-acetyl-Rhein II | 12.0 min |
| *Tri-acety-Aloemodine | 13.0 min |
| *Aloemodine | 13.5 min |
| Mono-acetyl-Rhein I | 15.5 min |
| Rhein | 20.0 min |
| *Tri-acetyl-Emodine | 21.0 min |
| 1,8-Danthrone | 43.0 min |
| *Emodine | 48.0 min |

*The amount of these impurities are lower than the limit of detection of HPLC-UV method. They are those assayed by more sensitive methods: HPLC using fluorimetric detection and LC-MS.

The specifications of the high purified non genotoxic Diacerein of the invention for the following impurities are:

| | |
|---|---|
| Mono-acetyl-Rhein II | Not more than 0.50% (our results from 0.11% to 0.21%) |
| Tri-acetyl-Aloemodine | Not more than 0.2 ppm (our results: absent) |
| Aloemodine | Not more than 1 ppm (our results from 0 to 1 ppm) |
| Mono-acetyl-Rhein I | Not more than 0.50% (our results from 0.0% to 0.22%) |
| Rhein | Not more than 0.20% (our results from 0.0% to 0.5%) |
| Tri-acetyl-Emodine | Not more than 0.1 ppm (our results: absent) |
| 1,8-Danthrone | Not more than 0.1 ppm (our results: absent) |
| Emodine | Not more than 1 ppm (our result from 0 to 1 ppm) |

Heavy Metals and Chromium
Heavy metals are determined by current USP or EP.
Chromium is determined by atomic absorption.
Equipment: Atomic absorption spectrometer
Technique: Flame
Lamp: Chromium hollow-cathode lamp
Flame type: Air-acetylene
Wavelengyh: 357.9 nm The specifications for the high purified non genotoxic Diacerein of the invention are the following:
Heavy metals: Not more than 10 ppm (our results from 5 to 8 ppm)
Chromium content: Not more than 5 ppm (our results from 2 to 4 ppm)
Residual Solvents Chromatography:
Column: DB-624 60 m, 0.32 mm ID, 1.8 µm
Detector: FID (flame ionization)
Carrier gas: Helium chromatographic grade
Column flow: 2.5 ml/min
Detector temperature: 250°
Injector temperature: 140°
Column temperature:

| Velocity<br>° C./min | Temperature<br>° C. | Time<br>Minutes |
|---|---|---|
| 0 | 40 | 10 |
| 20 | 250 | 5 |

Volume of injection: 1000 µl
Split ratio: 5
Run time: 26 min
Head Space Conditions Transfer line: 120° C.
Transfer line: 115° C.
Incubation time: 30 minutes The specifications for the high purified non genotoxic Diacerein of the invention are the following:

| | |
|---|---|
| N,N dimethylformamide | Not more than 500 ppm (our results from 50 to 300 ppm) |
| Acetone | Not more than 50 ppm (our results: absent) |
| Acetic acid | Not more than 50 ppm (our results from 0 to 20 ppm) |
| Ethanol | Not more than 50 ppm (our results: absent) |
| Triethylamine | Not more than 50 ppm (our result from 0 to 30 ppm |

The invention claimed is:

1. A process for producing non-genotoxic Diacerein, starting from raw Diacerein or raw Rhein, comprising the following successive steps:
   a. transforming raw Diacerein or raw Rhein into a water-soluble salt thereof; then
   b. dissolving said salt in water;
   c. adsorbing Diacerein or Rhein on a hydrophobic resin, by percolation of the aqueous solution obtained after step b. through a column filled with hydrophobic resin;
   d. after step c., desorbing the impurities using an organic solution, recovering the organic fractions which contain the impurities;
   e. after step d., desorbing Diacerein or Rhein using an hydro alcoholic solution, recovering the hydro alcoholic fractions which contain Diacerein or Rhein salt;
   f. acidifying the collected hydro alcoholic fractions recovered after step e.;
   g. recovering and drying non-genotoxic Diacerein.

2. The process according to claim 1, further comprising, after step f. and before step g., an additional step consisting in transforming Rhein in Diacerein by acetylation.

3. The process according to claim 1, wherein in step a. the water soluble salt is an inorganic salt.

4. The process according to claim 3, wherein in step a. the water soluble salt is a salt of an alkali metal.

5. The process according to claim 4, wherein in step a. the water soluble salt is a potassium salt or a sodium salt.

6. The process according to claim 1, wherein in step c. the hydrophobic resin is a copolymer of styrene and divinylbenzene (PS-DVB).

7. The process according to claim 6, wherein the copolymer of styrene and divinylbenzene (PS-DVB) is substituted on the benzene by halogen atoms.

8. The process according to claim 1, wherein in step c. the hydrophobic resin is porous.

9. The process according to claim 8, wherein the pore volume is above 1 ml/g.

10. The process according to claim 9, wherein the pore volume is between 1 ml/g and 2.5 ml/g.

11. The process according to claim 1, wherein in step c. the hydrophobic resin has a specific surface area, which is above 550 m$^2$/g.

12. The process according to claim 11, wherein the specific surface area, is between 550 m$^2$/g and 1300 m$^2$/g.

13. The process according to claim 12, wherein the specific surface area, is between 590 m$^2$/g and 1200 m$^2$/g.

14. The process according to claim 1, wherein in step c. the hydrophobic resin is under the form of particles, and the particle size range is from 50 μm to 700 μm.

15. The process according to claim 14, wherein the particle size range is between 250 μm and 700 μm.

16. The process according to claim 15, wherein the particle size range is between 250 μm and 600 μm.

17. The process according to claim 1, wherein in step c. the hydrophobic resin has a water retention capacity ranging from 40% to 70%.

18. The process according to claim 17, wherein the water retention capacity ranges from 45% to 55%.

19. The process according to claim 1, wherein in step c. the hydrophobic resin is a copolymer of styrene and divinylbenzene (PS-DVB); which is porous, which has a specific surface area above 550 m$^2$/g, which is under the form of particles and the particle size range is from 50 μm to 700 μm and which has a water retention capacity ranging from 40% to 70%.

20. The process according to claim 1, wherein step e. is repeated at least two times and each hydro alcoholic fraction is collected.

21. The process according to claim 1, wherein step e. is performed with the use of water/ethanol or water/methanol mixtures as elution solvent.

22. The process according to claim 1, wherein in step e. the alcohol/water mass ratio ranges from 10%/90% to 60%/40% (w/w).

* * * * *